United States Patent
Govari (10) Patent No.: US 10,869,713 B2
(45) Date of Patent: Dec. 22, 2020

(54) ABLATION POWER SUPPLY

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 697 days.

(21) Appl. No.: 15/656,227

(22) Filed: Jul. 21, 2017

(65) Prior Publication Data

US 2019/0021779 A1    Jan. 24, 2019

(51) Int. Cl.
*A61B 18/10* (2006.01)
*A61B 18/12* (2006.01)
*H02J 7/00* (2006.01)
*A61B 18/14* (2006.01)
(Continued)

(52) U.S. Cl.
CPC ...... *A61B 18/1206* (2013.01); *A61B 18/1233* (2013.01); *A61B 18/14* (2013.01);
(Continued)

(58) Field of Classification Search
CPC . A61B 18/1206; A61B 18/1233; A61B 18/14; A61B 18/1492; A61B 2017/00088; A61B 2017/00092; A61B 2018/00351; A61B 2018/00577; A61B 2018/00708; A61B 2018/00815; A61B 2018/00821; A61B 2018/00839; A61B 2018/00875; A61B 2018/1226; A61B 2018/1266;
(Continued)

(56) References Cited

U.S. PATENT DOCUMENTS 5,243,269 A * 9/1993 Katayama .......... H02J 1/10
                                                    307/66
5,449,380 A    9/1995 Chin
(Continued)

FOREIGN PATENT DOCUMENTS

DE    10 2010 003995 A1    7/2011
EP          1 187 296 A2    3/2002
EP          2 345 454 B1    5/2013

OTHER PUBLICATIONS

European Search Report and Written Opinion dated Nov. 30, 2018 for Application No. EP 18184624.7, 8 pgs.

*Primary Examiner* — Michael F Peffley
*Assistant Examiner* — Amanda L Zink
(74) *Attorney, Agent, or Firm* — Frost Brown Todd LLC (57) ABSTRACT

Apparatus, consisting of a power supply having a first electrical connection to a relatively high voltage source and connectable to ablation circuitry in a catheter via a second electrical connection. There are rechargeable first and second subsidiary power sources in the power supply. The apparatus also has a control unit, and a first switch alternately connecting the ablation circuitry to the first and second subsidiary power sources responsively to control signals from the control unit. The apparatus also has a second switch alternately connecting one of the first and second subsidiary power sources to the high voltage source for recharging thereof responsively to the control signals while the one of the first and second subsidiary power sources is disconnected from the ablation circuitry and another of the first and second subsidiary power sources is connected to the ablation circuitry by the first switch.

20 Claims, 5 Drawing Sheets

(51) Int. Cl.
*H02J 7/34* (2006.01)
*A61B 18/00* (2006.01)
*A61B 34/20* (2016.01)
*A61B 17/00* (2006.01)

(52) U.S. Cl.
CPC ........ *A61B 18/1492* (2013.01); *H02J 7/0013* (2013.01); *A61B 2017/00088* (2013.01); *A61B 2017/00092* (2013.01); *A61B 2018/00351* (2013.01); *A61B 2018/00577* (2013.01); *A61B 2018/00708* (2013.01); *A61B 2018/00815* (2013.01); *A61B 2018/00821* (2013.01); *A61B 2018/00839* (2013.01); *A61B 2018/00875* (2013.01); *A61B 2018/1226* (2013.01); *A61B 2018/1266* (2013.01); *A61B 2018/1273* (2013.01); *A61B 2034/2051* (2016.02); *A61B 2034/2072* (2016.02); *H02J 7/345* (2013.01)

(58) Field of Classification Search
CPC .... A61B 2018/1273; A61B 2034/2051; A61B 2034/2072; H02J 7/0013; H02J 7/345
See application file for complete search history.

(56) References Cited

U.S. PATENT DOCUMENTS

| | | |
|---|---|---|
| 5,766,153 A | 6/1998 | Eggers |
| 6,226,542 B1 | 5/2001 | Reisfeld |
| 6,288,521 B1 * | 9/2001 | Meador ................ H02J 7/0019 320/118 |
| 6,301,496 B1 | 10/2001 | Reisfeld |
| 6,814,733 B2 | 11/2004 | Schwartz |
| 6,892,091 B1 | 5/2005 | Ben-Haim |
| 6,997,924 B2 | 2/2006 | Schwartz |
| 7,156,816 B2 | 1/2007 | Schwartz |
| 7,536,218 B2 | 5/2009 | Govari |
| 7,756,576 B2 | 7/2010 | Levin |
| 9,153,994 B2 | 10/2015 | Wood et al. |
| 2003/0171745 A1 | 9/2003 | Francischelli |
| 2011/0172659 A1 * | 7/2011 | Brannan ............. A61B 18/1477 606/42 |
| 2014/0236138 A1 | 8/2014 | Tran |
| 2018/0099161 A1 * | 4/2018 | Honda ........... A61B 17/320092 |

* cited by examiner

ABLATION POWER SUPPLY

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to instruments for diagnostic and surgical purposes. More particularly, this invention relates to a switching arrangement for the supply or distribution of electric power in a medical instrument.

2. Description of the Related Art

Ablation of body tissue using electrical energy is known in the art. The ablation is typically performed by applying alternating currents, for example radiofrequency energy, to the electrodes, at a sufficient power to destroy target tissue. For example, procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions. Typically, the electrodes are mounted on the distal tip of a catheter, which is inserted into a subject.

Ablation power supplies that run from "wall" power have to be isolated to very high standards in order to protect the patient and the delicate electronics used in studies of cardiac physiology. This becomes costly when high power needs to be used. For example, one type of ablation may require 5 kW for 4 s (20 kJ). However, while other less highly powered systems may use power in the order of 100 W for longer time periods, even for these systems, achieving the desired isolation is expensive, for example due to labor intensive manufacturing costs.

SUMMARY OF THE INVENTION

Disclosed embodiments of the invention do away with the isolation requirement in an ablation catheter by running the power supply from a bank of capacitors, and/or from a battery. A typical system uses a pair of battery/capacitor banks, wherein one bank is always being charged. A control, typically a relay, ensures, via a pair of switches, that the banks toggle between being charged and delivering ablation power to the catheter. When the ablation circuitry is connected to the power-delivering bank, it is completely isolated from the wall power. The switching circuitry ensures that there is always power available to an ablation electrode and other catheter elements.

By using a pair of battery/capacitor banks, embodiments of the present invention ensure that the only power leakage that may affect the ablation catheter is from the switching circuitry, which is low powered. By reducing the possible power leakage through the catheter, insulation requirements for the power supply as a whole are substantially reduced.

Thus, an embodiment of the present invention provides apparatus, including:

a power supply having a first electrical connection to a relatively high voltage source and connectable to ablation circuitry in a catheter via a second electrical connection. There are rechargeable first and second subsidiary power sources in the power supply, and there is also a control unit. The apparatus also includes a first switch alternately connecting the ablation circuitry to the first and second subsidiary power sources responsively to control signals from the control unit, and a second switch alternately connecting one of the first and second subsidiary power sources to the high voltage source for recharging thereof responsively to the control signals while the one of the first and second subsidiary power sources is disconnected from the ablation circuitry and another of the first and second subsidiary power sources is connected to the ablation circuitry by the first switch.

In a disclosed embodiment the first switch and the second switch are double pole, double throw switches.

In a further disclosed embodiment the first switch and the second switch are ganged together.

In a yet further disclosed embodiment the first and second subsidiary power sources are batteries or capacitors.

In an alternative embodiment the first and second subsidiary power sources output a lower voltage than the high voltage source.

In a further alternative embodiment the high voltage source produces alternating current (AC) and the first and second subsidiary power sources produce direct current (DC). The apparatus further includes a direct current generator having an AC input linked to the high voltage source and a DC output linked to the first and second subsidiary power sources, and an alternating current generator having a DC input linked to the first and second subsidiary power sources and an AC output linked to the ablation circuitry.

In a yet further alternative embodiment the control unit is operative to unlink both of the first and second subsidiary power sources from the ablation circuitry and from the high voltage source.

Typically, the control unit is operative to concurrently link both of the first and second subsidiary power sources to the ablation circuitry and concurrently unlink both of the first and second subsidiary power sources from the high voltage source.

There is further provided, according to an embodiment of the present invention, a method, including:

providing a power supply having a first electrical connection to a relatively high voltage source and connectable to ablation circuitry in a catheter via a second electrical connection;

incorporating rechargeable first and second subsidiary power sources in the power supply;

providing a control unit;

alternately connecting, via a first switch, the ablation circuitry to the first and second subsidiary power sources responsively to control signals from the control unit; and alternately connecting, via a second switch, one of the first and second subsidiary power sources to the high voltage source for recharging thereof responsively to the control signals while the one of the first and second subsidiary power sources is disconnected from the ablation circuitry and another of the first and second subsidiary power sources is connected to the ablation circuitry by the first switch.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

The terms "link", "links", "couple" and "couples" are intended to mean either an indirect or direct connection. Thus, if a first device couples to a second device, that connection may be through a direct connection, or through an indirect connection via other devices and connections.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

Figure 1:
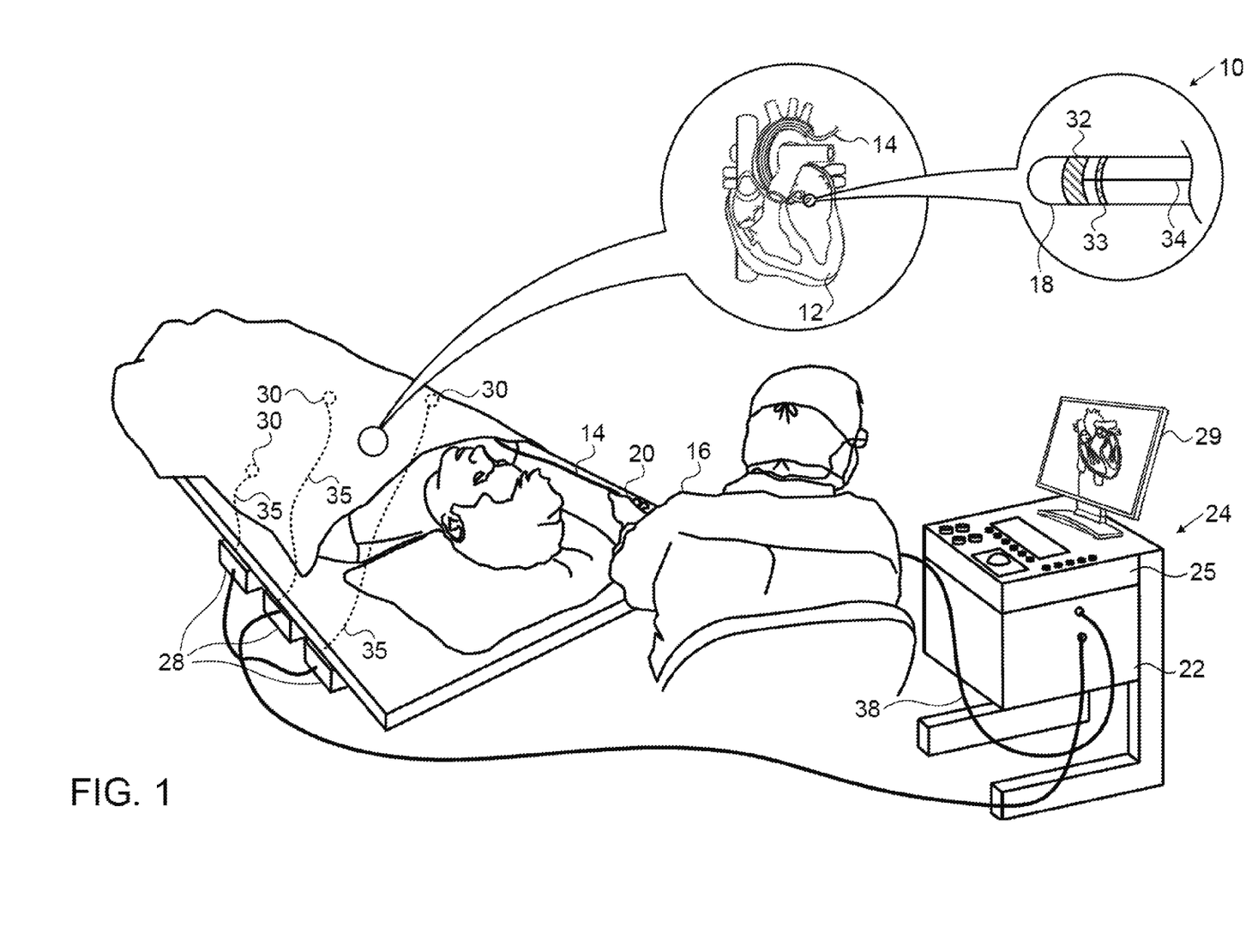
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system. The electrodes 32 and the body surface electrodes 30 may be used to measure tissue impedance at the ablation site as taught in U.S. Pat. No. 7,536,218, issued to Ovaria et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

Figure 2:
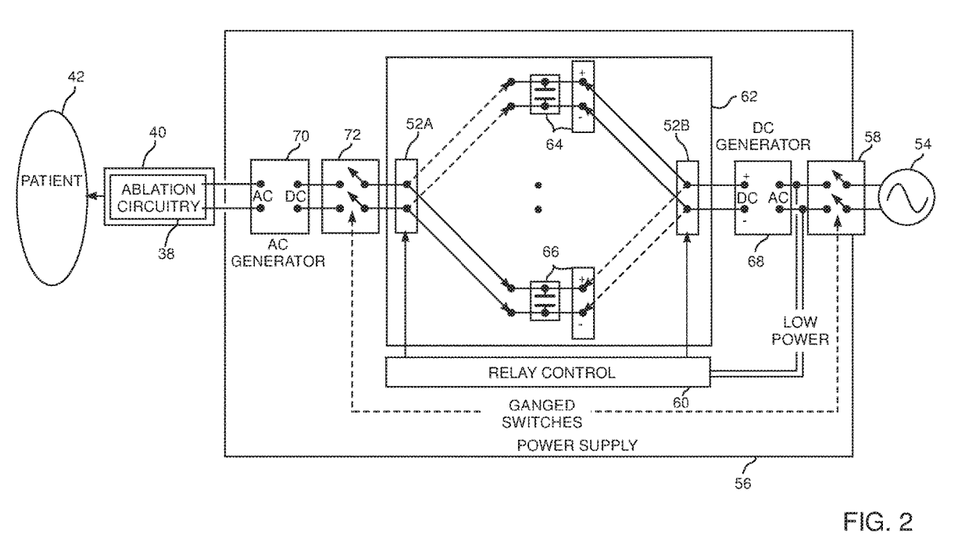
FIG. 2 is a schematic diagram of a power supply for a catheter in accordance with an embodiment of the invention.

Reference is now made to FIG. 2, which is a schematic diagram of an arrangement for powering a catheter having ablation circuitry, in accordance with an embodiment of the invention. A power source 54 supplies power to ablation circuitry 38 and other power requirements of a catheter 40, which is substantially similar to catheter 14 (FIG. 1), and which in operation is introduced into a patient 42. The power source 54 may be a relatively high voltage source of alternating current (AC), e.g., wall power of 120 V or 240 V. A power supply 56 for the catheter is enabled and disabled by a main power switch 58 that is connected to power source 54. In this and the following figures, electrical connections between elements are indicated by arrows formed by solid lines, and disconnections by arrows formed by broken lines.

Two subsidiary power sources, 64, 66, herein also termed power banks 64, 66, supply power to catheter 40, in particular to an ablation electrode and ablation circuitry 38 of the catheter, but also to other facilities in the catheter that may be required for electrophysiologic study of a subject's heart. Such facilities can include, but are not limited, to those noted in the description of FIG. 1. In any event, in some applications, it is important that power to such facilities be uninterrupted. The banks 64, 66, can be batteries, or capacitors, or combinations thereof. They are charged by a direct current (DC) generator 68, which in turn is supplied by alternating current from the source 54 when the main power switch 58 is closed. The voltage output of the DC generator is selected so that it is compatible with the operating voltage of the capacitors and with the output voltage of the batteries of banks 64, 66.

An alternating current generator 70 receives direct current, via a switch 72, from the banks 64, 66 and supplies alternating current to ablation circuitry 38. For the ablation by passage of radiofrequency electrical current referred to above, the alternating current may be supplied at a typical frequency used for ablation, such as approximately 10 kHz. The switch 72 is coupled to the catheter, and it may be ganged with the main power switch 58, enabling the banks 64, 66 to be simultaneously disconnected from the catheter and the power supply 56 from the source 54, for example on completion of a patient procedure.

A relay control unit 60, which draws low power from the source 54, controls a switching unit 62 that in turn controls connections between the banks 64, 66 and the generators 68, 70. Switching unit 62 comprises a pair of switches 52A, 52B, typically double pole, double throw (DPDT) switches, and relay control unit 60 is configured to provide signals so as to alternately connect the switches between banks 64, 66, and generators 68, 70, so that there is never a direct galvanic connection between the two generators (generator 70 supplying the catheter and generator 68 receiving power from source 54). From FIG. 2 it is apparent that the only possible electrical path between source 54 and the catheter is via relay control 60. Thus, insulation requirements for power supply 56, to ensure that there is no electrical leakage path between source 54 and the catheter, are only required to meet the low power requirements of the relay control unit. These insulation requirements are substantially less onerous, costing substantially less, than systems having insulation requirements where there is a direct path between source 54 and the catheter and its AC generator.

FIG. 2 illustrates power supply 56 in its "off" state, wherein switches 58 and 72 are both in an open, "off," state. Thus, there is no connection from source 54 to the power supply, and no connection from the power supply to the catheter. Because there is no connection from source 54 to the power supply, relay control 60 is inoperative, so that switches 52A, 52B do not change their state. By way of example, switch 52A is shown as being connected to bank 66, and switch 52B is shown as being connected to bank 64.

Figure 3:
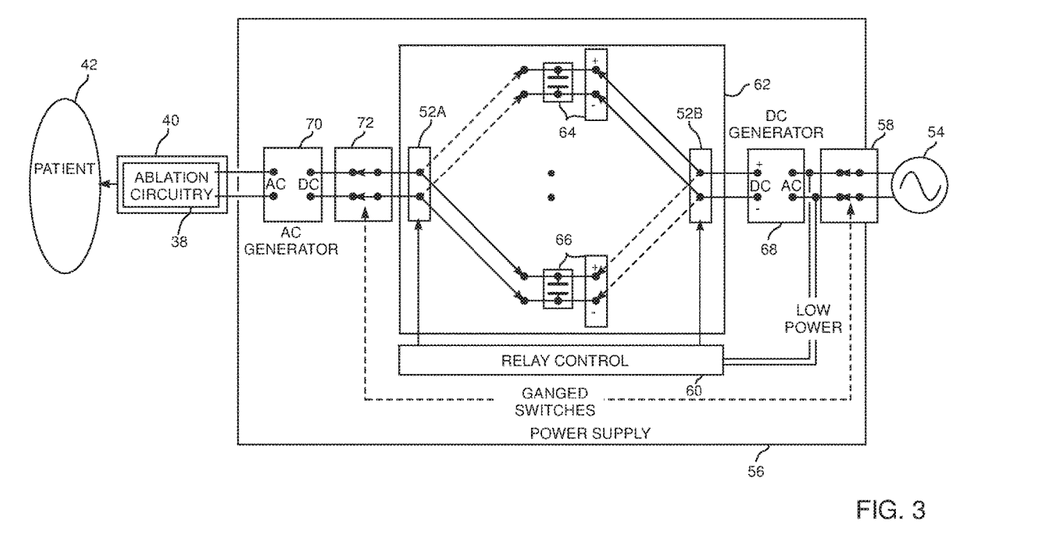
FIG. 3 is another schematic diagram of the power supply shown in FIG. 2 in accordance with an embodiment of the invention.
Figure 4:
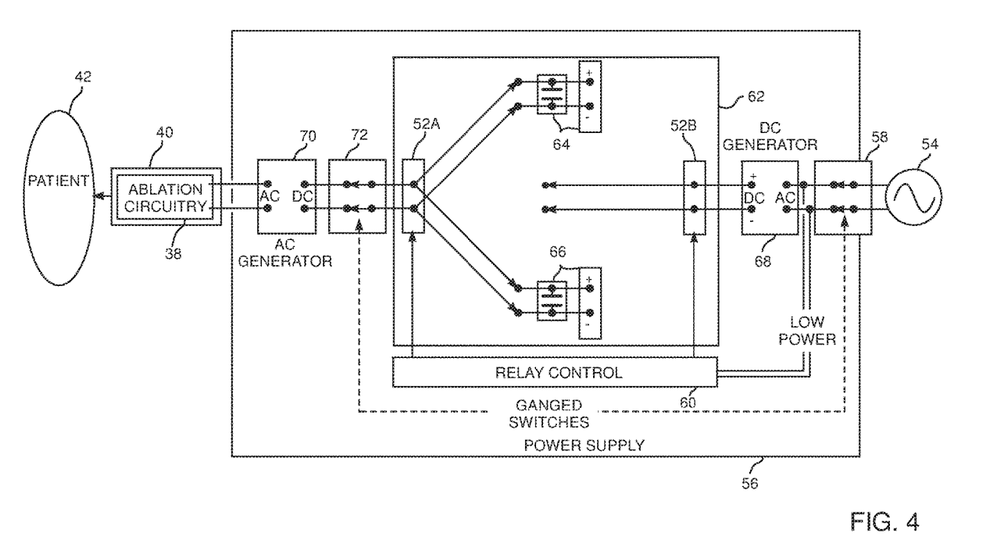
FIG. 4 is another schematic diagram of the power supply shown in FIG. 2 in accordance with an embodiment of the invention.
Figure 5:
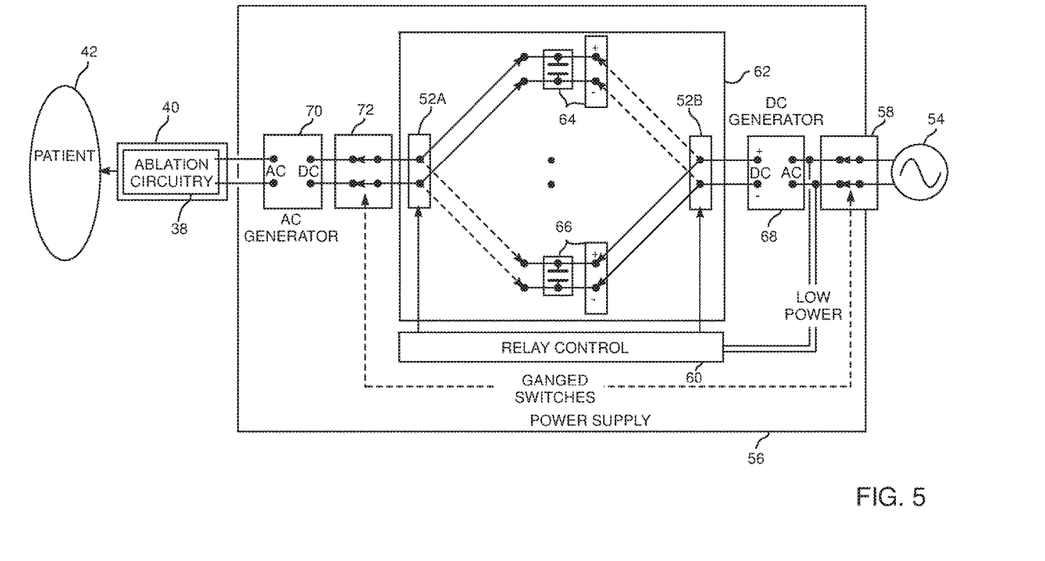
FIG. 5 is another schematic diagram of the power supply shown in FIG. 2 in accordance with an embodiment of the invention.

Reference is now made to FIGS. 3, 4, and 5, which illustrate different states of power supply 56 in its "on" state, in accordance with an embodiment of the present invention. In the on state of power supply 56 switches 58 and 72 are both in closed, "on," states. When the main power switch 58 is closed, the relay control unit 60 becomes active and is able to control the switching unit 62. In addition, AC power reaches the catheter from the generator 70, which is activated via switch 72, switch 72 having been closed when switch 58 closes. Furthermore, the switching unit 62 is versatile, and is capable of connecting one or both of the banks 64, 66 or neither of them to the generators 68, 70 in various combinations, as explained below.

FIG. 3 illustrates that in the on state of the power supply, generator 68 charges bank 64 via switch 52B, while switch 52B is disconnected from bank 66. While bank 64 is being charged, bank 66 supplies power to generator 70 via switch 52A, while switch 52A is disconnected from bank 64.

FIG. 4 is a schematic diagram of the power supply 56 during a reversal of the roles of the banks 64, 66. The main power switch 58 and switch 72 are closed, as described above for the on state of the power supply. Switch 52B of the switching unit 62 has disconnected both banks 64, 66 from the generator 68, so that the contacts of the switch are in an intermediate, open-circuit, state. Switch 52A has connected both banks 64, 66 to the generator 70. One of the banks 64, 66 is charged as a result of previous operation, and is able to supply power to the generator 70. The other one of the banks 64, 66 is typically discharged, but its state is immaterial at this stage. During the transition the catheter at no time is without power, yet is never exposed to the high voltages produced by the source 54, only to relatively low voltages of the banks 64, 66 and the generator 70. In addition, there is no path, except through relay 60, between source 54 and catheter 40.

FIG. 5 is a schematic diagram of the power supply 56 upon completion of a reversal of the roles of the banks 64, 66. It will be recalled that in FIG. 3, the bank 66 was powering the generator 70. Now the bank 66 is disconnected from the generator 70 and is being charged via switch 52B by the generator 68. Bank 64 is connected to and powering the generator 70 via switch 52A, but is disconnected from generator 68.

As stated above relay control 60 activates switches 52A, 52B, so that in the on state of the power supply, the power supply is in one of the states illustrated in FIGS. 3, 4, and 5. Typically control 60 is configured to monitor the state of banks 64 and 66 so as to toggle 52A, 52B according to the states of the banks. Thus when control 60 detects that a bank that is supplying power to the catheter has, or is about to be, discharged, the control toggles switches 52A, 52B so that the other, charged, bank supplies the catheter, and so that the discharged bank is charged.

While the description above has assumed a pair of double pole double throw switches (DPDT) 52A, 52B are operative in power supply 56, those having ordinary skill in the art will be aware that other arrangements of switches, performing the same functions as switches 52A, 52B, and equivalent to the pair of DPDT switches, may be used in the power supply. All such equivalent arrangements of switches are within the scope of the present invention.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:
   a power supply having a first electrical connection to a high voltage source and connectable to ablation circuitry in a catheter via a second electrical connection;
   rechargeable first and second subsidiary power sources in the power supply;
   a control unit;
   a first switch alternately connecting the ablation circuitry to the first and second subsidiary power sources responsively to control signals from the control unit; and
   a second switch alternately connecting one of the first and second subsidiary power sources to the high voltage source for recharging thereof responsively to the control signals while the one of the first and second subsidiary power sources is disconnected from the ablation circuitry and another of the first and second subsidiary power sources is connected to the ablation circuitry by the first switch.

2. The apparatus according to claim 1, the first switch and the second switch comprising double pole, double throw switches.

3. The apparatus according to claim 1, the first switch and the second switch being ganged together.

4. The apparatus according to claim 1, the first and second subsidiary power sources comprising batteries or capacitors.

5. The apparatus according to claim 1, the first and second subsidiary power sources being configured to output a lower voltage than the high voltage source.

6. The apparatus according to claim 1, the high voltage source being configured to produce alternating current (AC) and the first and second subsidiary power sources being configured to produce direct current (DC), further comprising:
   a direct current generator having an AC input linked to the high voltage source and a DC output linked to the first and second subsidiary power sources; and
   an alternating current generator having a DC input linked to the first and second subsidiary power sources and an AC output linked to the ablation circuitry.

7. The apparatus according to claim 1, the control unit being operative to unlink both of the first and second subsidiary power sources from the ablation circuitry and from the high voltage source.

8. The apparatus according to claim 1, the control unit being operative to concurrently link both of the first and second subsidiary power sources to the ablation circuitry and concurrently unlink both of the first and second subsidiary power sources from the high voltage source.

9. A method, comprising:
   providing a power supply having a first electrical connection to a high voltage source and connectable to ablation circuitry in a catheter via a second electrical connection;
   incorporating rechargeable first and second subsidiary power sources in the power supply;
   providing a control unit;
   alternately connecting, via a first switch, the ablation circuitry to the first and second subsidiary power sources responsively to control signals from the control unit; and
   alternately connecting, via a second switch, one of the first and second subsidiary power sources to the high voltage source for recharging thereof responsively to the control signals while the one of the first and second subsidiary power sources is disconnected from the ablation circuitry and another of the first and second subsidiary power sources is connected to the ablation circuitry by the first switch.

10. The method according to claim 9, the first switch and the second switch comprising double pole, double throw switches.

11. The method according to claim 9, the first switch and the second switch being ganged together.

12. The method according to claim 9, the first and second subsidiary power sources being batteries or capacitors.

13. The method according to claim 9, the first and second subsidiary power sources being configured to output a lower voltage than the high voltage source.

14. The method according to claim 9, the high voltage source producing alternating current (AC) and the first and second subsidiary power sources producing direct current (DC), further comprising:
   providing a direct current generator having an AC input linked to the high voltage source and a DC output linked to the first and second subsidiary power sources; and
   providing an alternating current generator having a DC input linked to the first and second subsidiary power sources and an AC output linked to the ablation circuitry.

15. The method according to claim 9, the control unit being operative to unlink both of the first and second subsidiary power sources from the ablation circuitry and from the high voltage source.

16. The method according to claim 9, the control unit being operative to concurrently link both of the first and second subsidiary power sources to the ablation circuitry and concurrently unlink both of the first and second subsidiary power sources from the high voltage source.

17. An apparatus, comprising:
- a power supply configured to couple a voltage source with an ablation circuitry;
- rechargeable first and second subsidiary power sources in the power supply, each of the first and second subsidiary power sources being configured to alternately source power to the ablation circuitry;
- a first switch alternately connecting the ablation circuitry to the first and second subsidiary power sources; and
- a second switch alternately connecting one of the first and second subsidiary power sources to the voltage source for recharging thereof while the one of the first and second subsidiary power sources is disconnected from the ablation circuitry and another of the first and second subsidiary power sources is connected to the ablation circuitry by the first switch, the first and second switches being configured to provide uninterrupted source power to the ablation circuitry during operation of the first switch.

18. The apparatus according to claim 17, the voltage source being configured to produce alternating current (AC) and the first and second subsidiary power sources being configured to produce direct current (DC), the apparatus further comprising:
- a direct current generator having an AC input linked to the voltage source and a DC output linked to the first and second subsidiary power sources; and
- an alternating current generator having a DC input linked to the first and second subsidiary power sources and an AC output linked to the ablation circuitry.

19. The apparatus according to claim 17, further comprising a control unit operable to control the first and second switches, the control unit being operative to unlink both of the first and second subsidiary power sources from the ablation circuitry and from the voltage source.

20. The apparatus according to claim 17, further comprising a control unit operable to control the first and second switches, the control unit being operative to concurrently link both of the first and second subsidiary power sources to the ablation circuitry and concurrently unlink both of the first and second subsidiary power sources from the voltage source.

* * * * *